(12) United States Patent  
Sookraj et al.

(10) Patent No.: US 11,827,590 B2  
(45) Date of Patent: Nov. 28, 2023

(54) ACRYLIC ACID, AND METHODS OF PRODUCING THEREOF

(71) Applicant: Novomer, Inc., Rochester, NY (US)

(72) Inventors: Sadesh H. Sookraj, Rochester, NY (US); Alexander Tseitlin, Rochester, NY (US)

(73) Assignee: Novomer, Inc., Rochester, NY (US)

( * ) Notice: Subject to any disclaimer, the term of this patent is extended or adjusted under 35 U.S.C. 154(b) by 195 days.

(21) Appl. No.: 17/152,248

(22) Filed: Jan. 19, 2021

(65) Prior Publication Data

US 2021/0139402 A1   May 13, 2021

Related U.S. Application Data

(63) Continuation of application No. 16/087,051, filed as application No. PCT/US2017/023302 on Mar. 21, 2017, now abandoned.

(Continued)

(51) Int. Cl.

| C07C 51/09 | (2006.01) |
| C07C 51/50 | (2006.01) |
| C07C 51/44 | (2006.01) |
| B01J 4/00 | (2006.01) |
| B01J 8/02 | (2006.01) |
| B01J 20/26 | (2006.01) |
| B01J 20/30 | (2006.01) |
| C07D 305/12 | (2006.01) |
| C08F 20/06 | (2006.01) |
| B01J 29/08 | (2006.01) |

(Continued)

(52) U.S. Cl.
CPC .............. *C07C 51/09* (2013.01); *B01J 4/001* (2013.01); *B01J 8/0278* (2013.01); *B01J 20/267* (2013.01); *B01J 20/3085* (2013.01); *B01J 29/084* (2013.01); *B01J 29/40* (2013.01); *C07C 51/44* (2013.01); *C07C 51/50* (2013.01); *C07D 305/12* (2013.01); *C08F 20/06* (2013.01); *C08F 120/06* (2013.01); *B01J 2208/00752* (2013.01)

(58) Field of Classification Search  
None  
See application file for complete search history.

(56) References Cited

U.S. PATENT DOCUMENTS 3,176,042 A * 3/1965 Schnizer ............... C07C 51/43  
562/599  
3,462,484 A  8/1969 Schnizer et al.  
(Continued)

FOREIGN PATENT DOCUMENTS

| CN | 1915957 A | 2/2007 |
| CN | 2009035508 A | 2/2009 |

(Continued)

OTHER PUBLICATIONS

Computer-generated English-language translation of JP-2013173088-A.*

(Continued)

*Primary Examiner* — Vu A Nguyen  
(74) *Attorney, Agent, or Firm* — Young Basile Hanlon & MacFarlane, P.C.

(57) ABSTRACT

Provided herein are methods of producing acrylic acid from beta-propiolactone. Such methods may involve the use of a heterogeneous catalyst, such as a zeolite.

17 Claims, 1 Drawing Sheet

Related U.S. Application Data

(60) Provisional application No. 62/311,262, filed on Mar. 21, 2016.

(51) Int. Cl.
*B01J 29/40* (2006.01)
*C08F 120/06* (2006.01)

(56) References Cited

U.S. PATENT DOCUMENTS

| | | | |
|---|---|---|---|
| 3,689,533 A | 9/1972 | Schultz et al. | |
| 3,849,457 A | 11/1974 | Haag | |
| 3,932,500 A * | 1/1976 | Duembgen | C07C 51/48 |
| | | | 203/68 |
| 5,198,578 A | 3/1993 | Etzkorn et al. | |
| 8,445,703 B2 * | 5/2013 | Allen | C07D 305/12 |
| | | | 549/328 |
| 8,796,475 B2 | 8/2014 | Allen et al. | |
| 8,961,909 B2 | 2/2015 | Lehr et al. | |
| 9,096,510 B2 | 8/2015 | Porcelli et al. | |
| 9,156,803 B2 | 10/2015 | Allen et al. | |
| 9,206,144 B2 | 12/2015 | Allen et al. | |
| 9,327,280 B2 | 5/2016 | Lee et al. | |
| 9,403,788 B2 | 8/2016 | Lee et al. | |
| 9,493,391 B2 | 11/2016 | Allen et al. | |
| 9,914,689 B2 | 3/2018 | Porcelli et al. | |
| 10,662,139 B2 * | 5/2020 | Sookraj | B01J 20/3085 |
| 2008/0161624 A1 | 7/2008 | Glover et al. | |
| 2010/0113822 A1 | 5/2010 | Craciun et al. | |
| 2011/0319849 A1 | 12/2011 | Collias et al. | |
| 2012/0123137 A1 | 5/2012 | Allen et al. | |
| 2012/0315681 A1 | 12/2012 | van Walsem et al. | |
| 2013/0165670 A1 | 6/2013 | Allen et al. | |
| 2013/0281715 A1 | 10/2013 | Allen et al. | |
| 2014/0275575 A1 | 9/2014 | Allen et al. | |
| 2014/0296522 A1 | 10/2014 | Lee et al. | |
| 2014/0309399 A1 | 10/2014 | Porcelli et al. | |
| 2015/0005513 A1 | 1/2015 | Lee et al. | |
| 2015/0141693 A1 | 5/2015 | Allen et al. | |
| 2015/0183708 A1 | 7/2015 | Harris et al. | |
| 2015/0299083 A1 | 10/2015 | Porcelli et al. | |
| 2015/0307437 A1 | 10/2015 | Ziemian et al. | |
| 2015/0368394 A1 | 12/2015 | Allen | |
| 2016/0016876 A1 | 1/2016 | Mahoney | |
| 2016/0102040 A1 | 4/2016 | Allen et al. | |
| 2016/0102068 A1 | 4/2016 | Allen et al. | |
| 2016/0288057 A1 | 10/2016 | Lapointe et al. | |
| 2017/0029352 A1 | 2/2017 | Sookraj et al. | |
| 2017/0073463 A1 | 3/2017 | Lee et al. | |
| 2017/0080409 A1 | 3/2017 | Farmer et al. | |
| 2017/0096407 A1 | 4/2017 | Sookraj | |
| 2017/0107103 A1 | 4/2017 | Sookraj et al. | |
| 2017/0145126 A1 | 5/2017 | Mahoney | |
| 2017/0225157 A1 | 8/2017 | Lee | |
| 2017/0247309 A1 | 8/2017 | Porcelli et al. | |
| 2017/0267618 A1 | 9/2017 | Sookraj et al. | |
| 2018/0016219 A1 | 1/2018 | Farmer et al. | |
| 2018/0022677 A1 | 1/2018 | Sookraj | |
| 2018/0029005 A1 | 2/2018 | Sookraj | |
| 2018/0030014 A1 | 2/2018 | Sookraj et al. | |
| 2018/0030015 A1 | 2/2018 | Farmer et al. | |
| 2018/0030201 A1 | 2/2018 | Farmer et al. | |
| 2018/0057619 A1 | 3/2018 | Sookraj | |
| 2018/0094100 A1 | 4/2018 | Farmer et al. | |
| 2018/0282251 A1 | 10/2018 | Sookraj | |

FOREIGN PATENT DOCUMENTS

| | | |
|---|---|---|
| CN | 103987682 A | 8/2014 |
| CN | 104350034 A | 2/2015 |
| CN | 106831389 A | 6/2017 |
| GB | 922177 A | 3/1963 |
| JP | S601205 A | 1/1985 |
| JP | S61213206 A | 9/1986 |
| JP | 2003173088 A | 6/2003 |
| JP | 2013173088 A * | 9/2013 |
| JP | 2013173088 A | 9/2013 |
| WO | 199407835 A1 | 4/1994 |
| WO | 2010/118128 A1 | 10/2010 |
| WO | 2012/030619 A1 | 3/2012 |
| WO | 2012134397 A1 | 10/2012 |
| WO | 2012/158573 A1 | 11/2012 |
| WO | 2013/063191 A1 | 5/2013 |
| WO | 2013/122905 A1 | 8/2013 |
| WO | 2013/126375 A1 | 8/2013 |
| WO | 2013185009 A1 | 12/2013 |
| WO | 2014/004858 A1 | 1/2014 |
| WO | 2014/008232 A2 | 1/2014 |
| WO | 2015/085295 A2 | 6/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 1/2016 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/023777 A1 | 2/2017 |
| WO | 2017/023820 A1 | 2/2017 |
| WO | 2017/165344 A1 | 9/2017 |
| WO | 2017/165345 A1 | 9/2017 |
| WO | 2017165323 A1 | 9/2017 |
| WO | 2018/085251 A1 | 5/2018 |
| WO | 2018/085254 A1 | 5/2018 |
| WO | 2018/136638 A1 | 7/2018 |
| WO | 2018/170006 A1 | 9/2018 |

OTHER PUBLICATIONS

International Search Report and Written Opinion received for PCT Patent Application No. PCT/US17/23302, dated Jun. 5, 2017, 9 pages.
Search Report for co-pending Taiwanese Application TW106109417; date of completion: Jul. 24, 2020; 6 pages.
Levy, Leon B., Journal of Polymer Science: Part A: Polymer Chemistry, vol. 30, 1992, 569-576.
Beta Analytic Testing Laboratory, Understanding Carbon-14 Analysis, Biobased Analysis—Radiocarbon Dating or carbon 14, dated Sep. 20, 2018 https://www.betalabservices.com/biobased/barconl4-dating.html <http://www.betalabservices.com/biobased/barconl4-dating.html> (2 pages).
Beta Analytic, published 2009 (Year: 2009).
Deactivation behavior, Nafe, Journal of Catalysis 329 (2015) 413-424.
Fan et al., Ethylene Formation by Catalytic Dehydration of Ethanol with Industrial Considerations, Materials, Dec. 28, 2012, pp. 101-115, vol. 6, Issue 1 (15 pages).
Levy, Leon B., Journal of Polymer Science: Part A: Polymer Chemistry, vol. 30, 1992, pp. 569-576.
Machine-generated English-language translation of JP2003173088A.
Potassium-Ion-Exchanged, Yan et al., ACS Catalysis (2017) 538-550.
Search Report for co-pending Taiwanese Application TW106109417; date of completion: Jul. 24, 2020; 7 pages.
International Search Report from co-pending PCT application PCT/US2019/039001, dated Nov. 7, 2019. Four pages.
Written Opinion of the ISA for co-pending PCT Application PCT/US2019/039001, dated Nov. 7, 2019. Nine pages.
Fujisawa et al., "One-Step Synthesis of w-Hydroxycarboxylic Acids By the Reaction Of w-Metaloxylated Grignard Reagents With ß-Propiolactones." Chemistry Letters, vol. 11, No. 4, 1982 (2 pages).
Kawashima et al., "A facile method for synthesis of three carbon-homologated carboxylic acid by regioselective ring-opening of ß-propiolactones with organocopper reagents, tetrahedron." vol. 45, Issue 2, 1989.

(56) References Cited

OTHER PUBLICATIONS

International Preliminary Report on Patentability for co-pending application PCT/US2019/039001, dated Dec. 29, 2020.
Chinese Office Action and Search Report for Application No. 201780018126, dated Apr. 16, 2021.
Japanese Office Action for Application No. 2018-549537, dated Mar. 9, 2021.
Zhu, Rui et al., "A Comprehensive Study on Metal Triflates Promoted Hydrogenolysis of Lactones to Carboxylic Acids: From Both Synthetic and Mechanistic Perspectives", ACS Catalysis, 2017, 7(11), 7520-7528, DOI: 10.1021/acscatal.7b01569.

* cited by examiner

ACRYLIC ACID, AND METHODS OF PRODUCING THEREOF

CROSS-REFERENCE TO RELATED APPLICATIONS

This application is a continuation of U.S. patent application Ser. No. 16/087,051 filed Sep. 20, 2018, which is a 371 of PCT/US2017/023302 filed Mar. 21, 2017, which claims benefit of U.S. Provisional Patent Application No. 62/311,262, filed Mar. 21, 2016, each of which is incorporated herein by reference in their entirety.

FIELD

The present disclosure relates generally to production of acrylic acid, and more specifically to production of acrylic acid from beta-propiolactone.

BACKGROUND

The production and use of acrylic acid (AA) has grown significantly in recent decades as the demand for polyacrylic acid-based superabsorbent polymers (SAPs) has grown. SAPs are used extensively for the manufacture of diapers, adult incontinence products, and feminine hygiene products, as well as in agricultural applications.

Currently, commercial acrylic acid is typically derived from propylene oxidation. Propylene is primarily a product of oil refining and its price and availability are closely tied to crude oil prices. Because of this, acrylic acid prices have risen dramatically in recent years. Thus, there exists a need in the art for alternative methods to synthesize acrylic acid.

BRIEF SUMMARY

Provided herein are methods of producing acrylic acid from beta-propiolactone. In some aspects, provided is a method of producing acrylic acid from beta-propiolactone, by combining beta-propiolactone, a heterogeneous catalyst, a polymerization inhibitor, and optionally a solvent; and producing acrylic acid from at least a portion of the beta-propiolactone. In some embodiments, the heterogeneous catalyst is a zeolite. In some variations, the zeolite is an acidic zeolite.

DESCRIPTION OF THE FIGURES

The present application can be best understood by reference to the following description taken in conjunction with the accompanying figures, in which like parts may be referred to by like numerals.

DETAILED DESCRIPTION

The following description sets forth exemplary methods, parameters and the like. It should be recognized, however, that such description is not intended as a limitation on the scope of the present disclosure but is instead provided as a description of exemplary embodiments.

Provided herein are methods of producing acrylic acid from beta-propiolactone using heterogeneous catalysts, such as zeolites. Such methods produce acrylic acid from beta-propiolactone in a one-pot reaction. Such methods may also produce acrylic acid in high yields, by minimizing other products that may form, such as polypropiolactone and polyacrylic acid.

Figure 1:
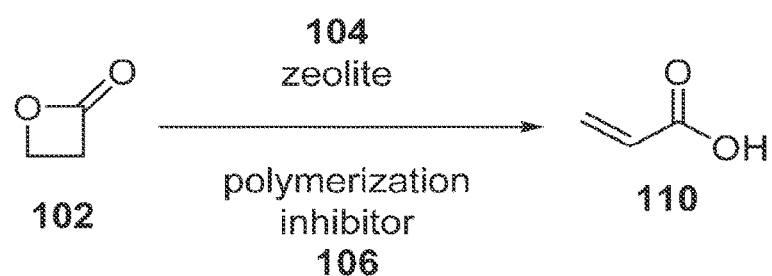
FIG. 1 depicts an exemplary process to produce acrylic acid from beta-propiolactone in the presence of a zeolite and a polymerization inhibitor.

In some aspects, provided is a method of producing acrylic acid from beta-propiolactone, by combining beta-propiolactone, a zeolite, and a polymerization inhibitor; and producing acrylic acid from at least a portion of the beta-propiolactone. For example, with reference to FIG. 1, process 100 is an exemplary process to produce acrylic acid. Beta-propiolactone 102 is combined with zeolite 104 and polymerization inhibitor 106 to produce acrylic acid 110. In some variations, process 100 is performed neat. In other variations, process 100 is performed in the presence of a solvent. In some embodiments, the method further includes continuously isolating the acrylic acid produced. In some variations, the acrylic acid isolated by distillation.

The beta-propiolactone, catalysts, polymerization inhibitors, solvents and reaction conditions, as well as acrylic acid produced, are described in further detail below.

Beta-Propiolactone (BPL)

In some embodiments, the beta-propiolactone used in the methods described herein may be produced by epoxide carbonylation. For example, the beta-propiolactone may be produced from ethylene oxide and carbon monoxide via a carbonylation reaction. See e.g., WO 2010/118128. In one variation, the beta-propiolactone is produced by reacting ethylene oxide with carbon monoxide in the presence of a carbonylation catalyst and optionally a solvent.

Suitable carbonylation catalysts are described in, for example, WO 2010/118128. For example, the carbonylation catalyst comprises [(TPP)Al][Co(CO)$_4$], [(ClTPP)Al][Co(CO)$_4$], [(TPP)Cr][Co(CO)$_4$], [(ClTPP)Cr][Co(CO)$_4$], [(salcy)Cr][Co(CO)$_4$], [(salph)Cr][Co(CO)$_4$], or [(salph)Al][Co(CO)$_4$]. It should generally be understood that "TPP" refers to tetraphenylporphyrin; "ClTPP" refers to meso-tetra(4-chlorophenyl)porphyrin); "salcy" refers to (N,N'-bis(3,5-di-tert-butylsalicylidene)-1,2-diaminocyclohexane); and "salph" refers to (N,N'-bis(salicylidene)-o-phenylenediamine).

In some variations, the beta-propiolactone is added to the reaction with an initial pressure of carbon monoxide. In other variations where the method is continuous, no initial pressure is required to add the beta-propiolactone.

Catalysts

In some embodiments, the catalyst used in the conversion of beta-propiolactone to acrylic acid is a heterogeneous catalyst. In certain variations, the catalyst is a zeolite. In one variation, the catalyst is an acidic zeolite. For example, the zeolite may be Zeolite Y or Zeolite ZSM-5.

In certain variations, the zeolite is Zeolite Y hydrogen in powder form. In one variation, the Zeolite Y hydrogen has a 80:1 mole ratio $SiO_2/Al_2O_3$, and has a powder surface area of 780 m$^2$/g.

The zeolite may be dried using any suitable methods or techniques known in the art (e.g., using heat and/or vacuum) prior to use.

A combination of any of the catalysts described herein may also be used.

Polymerization Inhibitors

In some embodiments, the polymerization inhibitor used in the conversion of beta-propiolactone to acrylic acid is a radical polymerization inhibitor. Suitable polymerization inhibitors may include, for example, phenothiazine.

Solvents

In some embodiments of the methods described herein, the conversion of beta-propiolactone to acrylic acid is performed neat. In other embodiments, the conversion of beta-propiolactone to acrylic acid is performed in the presence of a solvent.

In some variations, the solvent selected (i) dissolves, or at least partially dissolves, the beta-propiolactone, but does not react, or minimally reacts, with the beta-propiolactone; or (ii) has a high boiling point so that the acrylic acid produced may be distilled while solvent remains in the reactor, or a combination of (i) and (ii). In certain variations, the solvent is a polar aprotic solvent. For example, the solvent may be a high boiling polar aprotic solvent. In one variation, the solvent includes sulfolane.

The amount of solvent used may be varied to balance the metering of beta-propiolactone added and the overall concentration of reagents in the reaction mixture. For example, in one variation, the ratio of beta-propiolactone to solvent in the reaction is about 1:1.

The solvent may be dried using any suitable methods or techniques known in the art prior to use.

A combination of any of the solvents described herein may also be used.

Processing Conditions

The methods described herein may be carried out batchwise or continuously. Various factors may affect the conversion of beta-propiolactone to acrylic acid according to the methods described herein.

For example, the rate of beta-propiolactone addition may affect the yield of acrylic acid. In some variations, the method further includes controlling the rate of addition of beta-propiolactone. A slower rate of beta-propiolactone addition was unexpectedly observed to increase the yield of acrylic acid produced. In some variations of the methods described herein, the beta-propiolactone is provided at a rate of less than 1.5 g/min, less than 1.4 g/min, less than 1.3 g/min, less than 1.2 g/min, less than 1.1 g/min, less than 1 g/min, less than 0.9 g/min, or less than 0.8 g/min; or between 0.5 g/min and 1.5 g/min, or between 0.75 g/min and 1.25 g/min; or about 1 g/min.

A slower rate of beta-propiolactone addition was also unexpectedly observed to reduce the amount of other products formed, such as polypropiolactone and polyacrylic acid. In some variations, the method further includes minimizing or suppressing production of polypropiolactone from at least a portion of the beta-propiolactone. In one variation, little or no polypropiolactone is produced. In other variations that may be combined with the foregoing, the method further includes minimizing or suppressing production of polyacrylic acid from at least a portion of the acrylic acid produced. In one variation, little or no polyacrylic acid is produced.

The amount of beta-propiolactone added may be metered by any suitable methods or techniques in the art. For example, beta-propiolactone may be metered or slowly added to the reactor via a needle valve.

The removal of acrylic acid produced may also affect the yield of acrylic acid. Stripping off of the acrylic acid produced was also unexpectedly observed to increase yield of the acrylic acid produced. In some variations, the method further includes stripping off at least a portion of the acrylic acid produced by distillation). In certain variations of the foregoing, stripping off at least a portion of the acrylic acid produced minimizes polymerization of the acrylic acid, and thus, formation of polyacrylic acid.

In some embodiments, the acrylic acid may be produced at a pressure that strips off of at least a portion of the acrylic acid produced. For example, in one variation, the method may be performed at subatmospheric pressure of 100 mm Hg. In other variations, vacuum may be applied in the range of 200 to 20 mm Hg.

The acrylic acid may be produced at elevated temperatures according to the methods described herein. In some embodiments, the temperature is at least 100° C., at least 105° C., at least 110° C., at least 115° C., at least 120° C., at least 125° C., at least 130° C., at least 135° C., at least 140° C., at least 145° C., at least 150° C., at least 155° C., at least 160° C., at least 165° C., at least 170° C., at least 175° C., at least 180° C., at least 185° C., at least 190° C., at least 195° C., at least 200° C., at least 205° C., at least 210° C., at least 215° C., or at least 220° C.; or between 100° C. and 220° C., or between 170° C. and 200° C. In some variations, the reactor in which the method is performed is heated to the temperatures described herein. In other variations, the beta-propiolactone, polymerization inhibitor, catalyst, and/or solvent is provided to the reactor at the temperatures described herein.

Acrylic Acid

In some embodiments of the methods described herein, acrylic acid is produced at a yield of at least 50%, at least 55%, at least 60%, at least 65%, at least 70%, at least 75%, at least 80%, at least 85%, at least 90%, or at least 95%.

In some embodiments of the methods described herein, the acrylic acid produced has a purity of at least 95%, at least 96%, at least 97%, or at least 98%. In some variations where the acrylic acid produced is isolated, e.g., by distillation, the acrylic acid has a purity of at least 98%, at least 98.5%, at least 99%, at least 99.1%, at least 99.2%, at least 99.3%, at least 99.4%, at least 99.5%, at least 99.6%, at least 99.7%, at least 99.8%, or at least 99.9%.

Downstream Products

The acrylic acid produced according to the methods described herein may be used for various applications. For example, acrylic acid may be used to make polyacrylic acid for superabsorbent polymers (SAPs). The SAPs find use in diapers, adult incontinence products, and feminine hygiene products among other things.

In some aspects, provided is a method for producing a superabsorbent polymer, by: polymerizing the acrylic acid produced according to any of the methods described herein in the presence of a cross-linker to produce the superabsorbent polymer.

Acrylic Acid Production Systems

Figure 2:
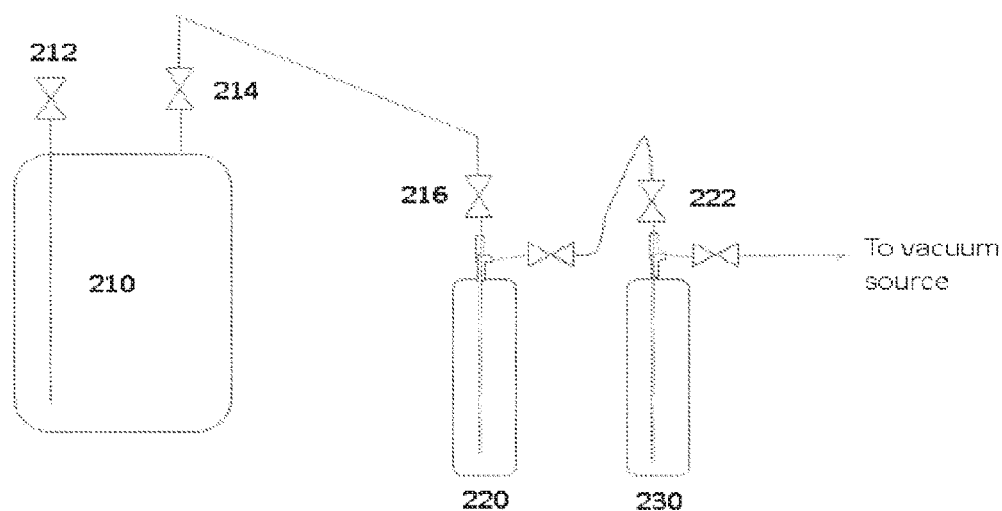
FIG. 2 depicts an exemplary reaction system to produce acrylic acid from beta-propiolactone according to the methods described herein.

In other aspects, provided herein are systems for production of acrylic acid. For example, with reference to FIG. 2, an exemplary acrylic acid production system is depicted. System 200 is configured to produce acrylic acid from beta-propiolactone, according to the methods described herein.

System 200 includes reactor 210, configured to receive beta-propiolactone, a zeolite, and a polymerization inhibitor, and to produce acrylic acid from at least a portion of the beta-propiolactone according to the methods described herein. Reactor 210 is configured to produce acrylic acid at an elevated temperature. Any of the temperatures described herein for the methods may be employed in the system. For example, in one variation, reactor 210 is configured to produce acrylic acid at a temperature between 170° C. and 200° C. Suitable reactors may include, for example, a Parr reactor.

In some variations, reactor 210 is configured to control the rate of addition of one or more of the beta-propiolactone, the zeolite, and the polymerization inhibitor added. For example, in one variation, a mixture of the beta-propiolactone and the polymerization inhibitor may be slowly added using a needle valve to a mixture of catalyst in a solvent.

With reference again to FIG. 2, reactor 210 further includes vapor port 214. In some variations, reactor 210 is configured to continuously strip off at least a portion of the acrylic acid produced, and vapor port 214 is configured to pass acrylic acid vapors to collection vessel 220.

With reference again to FIG. 2, system 200 further includes acid/base scrubber 230, configured to receive acrylic acid from collection vessel 220. In other variations of the system, acid/base scrubber 230 may be omitted. Further, with reference to FIG. 2, elements 212, 216 and 222 are dip tubes.

The systems provided herein may be configured for batch-wise or continuous production of acrylic acid.

EXAMPLES

The following Examples are merely illustrative and are not meant to limit any aspects of the present disclosure in any way.

Example 1

Conversion of Beta-Propiolactone to Acrylic Acid Using a Zeolite

This Example demonstrates the production of acrylic acid from beta-propiolactone using a zeolite.

A mixture of beta-propiolactone (3.0 g) and phenothiazine (9.0 mg) was added using a needle value to a mixture of sulfolane (40.0 g) and Zeolite Y hydrogen (20.0 g) at 165° C. with 50 psi of carbon monoxide. Zeolite Y hydrogen (80:1 mole ratio $SiO_2/Al_2O_3$, powder S.A. 780 $m^2$/g) was dried under vacuum at 100° C. for one day before use. Phenothiazine was the polymerization inhibitor used. Sulfolane was the solvent used, and was dried over 3 Å molecular sieves prior to use. The beta-propiolactone was added slowly using the needle valve over about 8.6 minutes. The reaction mixture was heated to 170° C. to produce acrylic acid.

The reaction was monitored by infrared spectroscopy (IR). The reaction was observed to be completed after about 3 hours, when no beta-propiolactone was detectable by IR. The zeolite was then filtered off from the reaction mixture, and a sample of the resulting mixture was dissolved in deuterium ($D_2O$) and chloroform ($CDCl_3$) for nuclear magnetic resonance (NMR) analysis. The observed vinyl peaks between δ 5.80 and 6.47 ppm in the $^1H$ NMR confirmed the production of acrylic acid.

What is claimed is:

1. A method of producing acrylic acid from beta-propiolactone, comprising:
   combining beta-propiolactone, a zeolite, and a polymerization inhibitor;
   producing acrylic acid from at least a portion of the beta-propiolactone;
   wherein the beta-propiolactone, the polymerization inhibitor, and the zeolite are combined neat or with a polar aprotic solvent; and wherein the produced acrylic acid has a purity of at least 95% and a yield of at least 90%.

2. The method of claim 1, the zeolite is an acidic zeolite.

3. The method of claim 1, wherein the zeolite is Zeolite Y or Zeolite ZSM-5, or a combination thereof.

4. The method of claim 1, wherein the polymerization inhibitor is phenothiazine.

5. The method of claim 1, wherein the acrylic acid produced is continuously isolated.

6. The method of claim 1, wherein the acrylic acid is produced at a temperature of between 170° C. and 200° C.

7. The method of claim 1, wherein the beta-propiolactone, the polymerization inhibitor, and the zeolite are further combined with the polar aprotic solvent.

8. The method of claim 7, wherein the polar aprotic solvent comprises sulfolane.

9. The method of claim 1, wherein the acrylic acid produced has a purity of greater than 95%.

10. The method of claim 1, further comprising isolating acrylic acid.

11. The method of claim 10, wherein the acrylic acid is isolated by distillation.

12. The method of claim 1, further comprising contacting an epoxide compound with carbon monoxide to form beta-propiolactone.

13. A method of producing acrylic acid from beta-propiolactone, comprising:
    contacting epoxide compound and carbon monoxide to form beta-propiolactone,
    combining beta-propiolactone, a zeolite, a polymerization inhibitor, and a polar aprotic solvent;
    producing acrylic acid from at least a portion of the beta-propiolactone;
    wherein the epoxide compound comprises ethylene oxide; and wherein the produced acrylic acid has a purity of at least 95% and a yield of at least 90%.

14. The method of claim 13, wherein the zeolite comprises Zeolite Y, and the solvent comprises sulfolane.

15. The method of claim 12, wherein the epoxide compound comprises ethylene oxide.

16. The method of claim 1, further comprises stripping off at least a portion of the acrylic acid produced.

17. The method of claim 1, wherein the beta-propiolactone, the polymerization inhibitor, and the zeolite are combined neat.

* * * * *